(12) United States Patent
Veal (10) Patent No.: US 11,313,832 B2
(45) Date of Patent: Apr. 26, 2022

(54) WEAR RESISTANT STREAMING CURRENT MEASUREMENT FLOW CELL WITH PISTON CENTERING

(71) Applicant: Charles R. Veal, Gainesville, GA (US)

(72) Inventor: Charles R. Veal, Gainesville, GA (US)

( * ) Notice: Subject to any disclaimer, the term of this patent is extended or adjusted under 35 U.S.C. 154(b) by 275 days.

(21) Appl. No.: 16/602,954

(22) Filed: Jan. 2, 2020

(65) Prior Publication Data
US 2021/0208100 A1 Jul. 8, 2021

(51) Int. Cl.
*G01N 27/60* (2006.01)
*G01N 33/18* (2006.01)

(52) U.S. Cl.
CPC ......... *G01N 27/60* (2013.01); *G01N 33/1893* (2013.01)

(58) Field of Classification Search
CPC ........................... G01N 27/60; G01N 33/1893
USPC ........................................................ 324/453
See application file for complete search history.

(56) References Cited

U.S. PATENT DOCUMENTS

| | | | | |
|---|---|---|---|---|
| 5,706,082 A | * | 1/1998 | Colgan | G01N 27/628 356/311 |
| 5,818,580 A | * | 10/1998 | Murnick | G01N 21/171 356/311 |
| 8,595,020 B2 | * | 11/2013 | Marino | G06Q 50/00 705/1.1 |
| 2002/0113597 A1 | * | 8/2002 | Veal, Jr. | G01N 27/60 324/453 |
| 2014/0202542 A1 | * | 7/2014 | LaRocque | C02F 1/008 137/613 |

\* cited by examiner

*Primary Examiner* — Christopher P McAndrew
(74) *Attorney, Agent, or Firm* — Laurence P. Colton; Smith Tempel Blaha LLC (57) ABSTRACT

A streaming current measurement flow cell, free from potential piston-to-electrode contact, with a flexible, but close-fitting piston and sleeve set, wherein a housing-defined bushing, as it encircles the piston's active segment near its upper end, does so with a short, cylindrical sidewall, the inside diameter of which, in comparison to the active segment's diameter, creates a narrower—but by only 0.002 inch—capillary-sized flow channel between the bushing and the active segment than exists between it and the sleeve. Even so, physical contact between piston and sleeve—a major wear factor—is completely eliminated; and larger particles known to scratch/gouge dielectric surfaces are kept out of the piston/sleeve flow channel. Moreover, a limitation on the piston's downward travel wherein the active segment's upper end is brought just flush with the upper electrode's flat, annular face makes possible a novel system, critical in self-cleaning this electrode where its inner edge and setback are exposed atop the bushing.

6 Claims, 5 Drawing Sheets

WEAR RESISTANT STREAMING CURRENT MEASUREMENT FLOW CELL WITH PISTON CENTERING

FIELD OF THE INVENTION

This invention relates to streaming current detectors, and more particularly, to an improved measurement flow cell, operable in either an on-line or off-line (batch) mode, with the flow cell having a close-fitting, but flexible piston and sleeve set in which the piston, as it is being reciprocated, is constrained by a short, piston-centering guide that negates the piston's characteristic side-to-side wobble, a motion which eventually would—if left unchecked during such a piston's routine, continuous operation—bring the piston's active segment into direct contact with the inner sidewall of the sleeve and possibly with that of a contiguous metal electrode as well, so that the flow cell, with its piston so constrained, is freed from premature wear and tear on the cell's streaming current signal-generating elements.

BACKGROUND OF THE INVENTION

Except for streaming current measurement flow cells in which the piston's active segment, between its distal ends, defines from four to six spaced apart, longitudinally extending lands, each contiguous pair of which bounds two sides of an elongated capillary-sized flow channel which itself is lined, opposite that portion of the active segment situated between said pair of lands, with the inner sidewall of a bore through which the active segment is reciprocated during use, no other flow cell with a piston-centering guide which is disposed on the active segment itself is known in the prior art.

Alternately, except for flow cells that have at least one piston-centering guide, one of which is disposed contiguous with the flow cell's sleeve and defines a bore of the same inside diameter as that of the sleeve, with these two bores being perfectly aligned, one with the other, when the sleeve and the guide contiguous therewith are disposed in assembled relation, no other flow cells which have both a sleeve and a piston-centering guide configured to simultaneously encircle different portions of a piston's active segment—whether lands-free or not—are known in the prior art.

A flow cell having as its piston-centering guide six lands arrayed strategically around the periphery of an active segment and extending the length thereof is taught by Bryant and Veal in U.S. Pat. Nos. 4,769,608 and 5,119,029. In this prior art device, the lands slideably engage not only the bore's cylindrical inner sidewall, but also a pair of identical ring electrodes, fitted into grooves formed therein and spaced apart from each other by approximately the length of the active segment. Each of these ring electrodes, which has the same inner diameter as does the bore's cylindrical inner sidewall, is mounted flush with it, leaving only an inwardly directed, circular face of a thin band of metal to be slideably engaged by the lands.

Otherwise, without each of these ring electrodes having its inwardly-directed, circular face so flush mounted, those skilled in the art of streaming current detectors would expect to find, while a modified version of this prior art device with non-flush mounted electrodes was operating, that a rapid buildup of contaminates on both of the electrodes, as well as on any surface disposed contiguous with either of them, was occurring/had occurred. Moreover, it is well known that when such a buildup does in fact occur, the streaming current cannot be reliably measured. Indeed, Bryant and Veal found that even though the electrodes present were flush mounted, they underwent a slow fouling over time which necessitated their being cleaned periodically.

Seeking a remedy so that users of a streaming current detector equipped with flush-mounted electrodes can avoid cleaning them and thus be spared from costly shutdowns of the process they may be using the detector to regulate, Bryant and Veal invented a slideably removable electrode holder. As disclosed in their '029 patent, a pair of electrodes so mounted, as well as the dielectric surface contiguous with them in the holder—a structure which defines the bore's cylindrical inner sidewall for its entire length—can be removed and replaced in less than one minute. In making this exchange so quickly, however, the installer is forced to leave the piston "as is", even though the active segment and especially the lands thereon may have been worn or otherwise degraded to such an extent as to warrant a substantially more time-consuming procedure in which both the electrode holder and the piston are removed and then replaced—with each of them in its respective "original" condition.

Upon also recognizing that the rate at which the electrodes erode, as well as the likelihood of their breaking or becoming dislodged, increased whenever the electrodes were mounted within the region where the piston's active segment slideably engaged the bore's cylindrical inner sidewall, Veal then invented a streaming current measurement flow cell in which the mounting of each of its electrodes is one that eliminates any possibility of the reciprocating piston slideably engaging such an electrode during use. Moreover, once he had mounted both electrodes outside of said region, Veal found away to reconfigure the flow cell's dielectric elements as well—or at least rework the structures that defined the cylindrically-shaped, slideably engageable surfaces upon which such dielectric elements depend, so that they could be replaced independently not only of each other, but also of the electrodes.

Even though with the flow cell which he disclosed in U.S. Pat. No. 6,515,481, Veal veered away from the use of a piston fettered in any fashion whatsoever with lands and opted instead to utilize as this prior art flow cell's piston, an elongated, waist-free and initially unmarred cylindrical column, he continued to rely—as did everyone else skilled in the art of streaming current measurement at that time—on "tried and true" design criteria for the flow cell's dielectric elements interacting as a whole. Under these criteria, said elements, in assembled relation, are to be aligned with each other in such a way as to maintain, in between the piston's active segment and any dielectric element slideably engageable therewith, an undiversified annulus—that is, a portion of space in the shape of an elongated, thin, cylindrical shell of uniform transverse cross-section. Moreover, this undiversified annulus is to extend throughout the length of the region in which the piston's active segment, during use, slideably engages any cylindrically shaped surface—whether it has dielectric properties or, like a ring electrode's inwardly directed face, lacks them.

Indeed, theorists have long advocated for the continued use of "the proper cylindrical sensor geometry"—that is, an alignment of the flow cell's dielectric elements which maintains the undiversified annulus—on the grounds that by basing their mathematical analyses on said geometry, they have been able to derive an essentially linear relationship between the streaming current and the zeta potential. (The latter can be obtained experimentally by a well-known, but time-consuming method, as explained by Canzoneri in U.S. Pat. No. 4,416,435.) With this linear relationship so derived at hand, one can then accurately predict the streaming current generated by an aqueous test sample, provided he also takes into account, along with other dimensions of the flow cell, the "gap-size" of its undiversified annulus as well as the test sample's temperature and viscosity. (The calculations such a prediction is based on are detailed by C. Walker et al. in "The Streaming Current Detector: A Quantitive Model", Journal of Colloid and Interface Science 182, 71-81 (1996).)

As far as the flow cell which Veal disclosed in the '481 patent is concerned, the structures that define this prior art instrument's dielectric elements are the piston's lands-free active segment, a removable sleeve and a dual function stop against which the upper end of the sleeve abuts in assembled relation. Consistent with said design criteria that call for the flow cell's dielectric elements to be aligned in such a way as to maintain the undiversified annulus, Veal provided the sleeve and the stop with matching inside diameters and sculpted the flow cell's housing—of which the stop is an integral part—so that once the sleeve has been slideably received within this housing and is held in abutment with the stop, the respective bores of the stop and sleeve are perfectly aligned. Thus, during use, they not only encircle different portions of the piston's active segment, but also variously interact with it, even as wear consumes both piston and sleeve.

Just how significant wear can be that alters the flow channel between the sleeve and the piston's active segment or, alternately, between this active segment and the dual function stop—with a clearance between each such stationary dielectric element and the reciprocating piston's active segment that initially measures about 0.005 inch—came to the fore for Veal when he discovered that prior art flow cells in which the upper electrode was configured and mounted as taught in the '481 patent were unexpectedly losing their capacity to generate a strong enough streaming current signal to be of use in large scale industrial processes. This problem stemmed, at least in part, from the fact that wear, occasioned by the piston's active segment rubbing against the inner sidewall of the sleeve during the piston's routine, continuous operation, had not only increased the "gap-size" of the initially undiversified annulus, but had also otherwise altered the annulus so that it no longer sported the uniform transverse cross-section it had had in the flow cell's "original" state. Exacerbating this problem was the fact that operators, faced with the presence of grit and silt or other large particles in the test fluid, would opt, at the outset, to utilize a flow cell with a "loose-fitting" sleeve/piston pair, only to find that the sensitivity of the streaming current detector, already reduced by their choice of said pair, was inadequate once significant wear on the "loose-fitting" pair's workings had taken place.

In order to remedy this situation for those without the technical know-how to adjust the strength of the streaming current signal by manipulating the detector's electronic components, Veal redesigned the flow cell which he had earlier disclosed in U.S. Pat. No. 6,515,481. Specifically, he replaced the upper electrode in this flow cell with a thin-edged, large diameter stainless steel disc that has an inside diameter which matches that of both the flow cell's removable sleeve and its stop. Upon mounting this disc-like electrode atop the stop, he axially aligned the respective inner edges of three flow cell components: the replacement electrode, the stop, and the sleeve. In so doing, he had effectively extended the prior art flow cell's undiversified annulus by the thickness of the replacement electrode's inner edge and found that the redesigned flow cell did in fact generate a stronger streaming current signal. Unfortunately, throughout such a flow cell's use—during which the piston, operating continuously year round, is typically moved up and down approximately four times per second, 24 hours per day, metal-to-plastic contact between the inner edge of the replacement electrode and the piston's active segment is always possible, greatly shortening the piston's useful life, once such contact occurs.

On the other hand, even those with said technical know-how have faced their own set of stumbling blocks when it comes to adjusting the strength of a streaming current signal. Adding to the complexity of doing such an adjustment in the field is the fact that when the flow cell has undergone physical wear, it should first be recalibrated, with the recalibration being carried out in as short a period of time as possible in order to keep the streaming current detector's downtime to a minimum. While methods exist, as taught by Dentel in U.S. Pat. No. 5,220,283, for recalibrating streaming current measurement flow cells/probes following physical wear that has altered the piston-bore gap distance and resulting probe sensitivity, none of the prior art flow cells/probes has included any of the isolation valves, sample ports and titration ports that would make it practicable for an operator to recalibrate such a flow cell/probe in place—that is, by turning off such valves fixedly attached to the flow cell's housing that would otherwise fluidly connect it to the test flow stream, so that the flow cell's recalibration can be carried out without dismantling any of the plumbing and/or disconnecting any hoses used, during routine operations, to feed the test flow stream into and out of the flow cell.

From the perspective of waterworks plant operators, just how one is to interpret streaming current signals, especially those generated in rapidly changing water conditions, has been a major challenge for decades. In such a situation, the dosage of the metal coagulant and/or polymer needed to properly treat raw water as it comes into the plant may change abruptly—sometimes within a half hour or less. A timely response would require the operator to immediately recognize the need to reset such a plant's metal coagulant/polymer dosage controlling set point—a predetermined quantity strongly dependent upon the density and nature of the charge-bearing colloids present in the raw water source preceding that of the latest incoming raw water flow—and then perform a prompt jar test. Unfortunately, when the operator has had to rely upon a prior art flow cell to help him run such a test, the test has taken at least 30 minutes to complete—a time period during which additional changes to the water quality of the incoming raw water may have occurred, thus potentially necessitating still further revisions to the set point.

Since colloids in untreated raw water generally bear negative charges and coagulation is a process designed to destabilize the colloids by reducing the repulsive, electrostatic forces between them, one can expect the streaming current to become less negative as coagulation progresses. Nevertheless, in the event an operator were to inadvertently reverse the polarity of the streaming current signal—which an individual in a hurry to replace an easily disposable lower electrode mounted on a retaining fitting in a prior art flow cell as taught by Veal in U.S. Pat. No. 6,515,481 might do, such an operator, still unaware of the polarity reversal, could misinterpret the positive streaming current signal in a variety of ways. For example, if the positive streaming current had reached a near zero value, it would most likely indicate that a satisfactory finished water quality had been achieved. On the other hand, a positive streaming current well above zero would be cause for alarm since such a signal would likely communicate that a charge reversal had occurred and enough colloidal particles had been reestablished in the treated water to give it a decidedly unfinished water quality.

SUMMARY OF THE INVENTION

An object of the present invention is to provide a streaming current measurement (SCM) flow cell having a flexible, but close-fitting piston and sleeve set in which the piston, as it reciprocates, interacts with a piston-centering guide/bushing in such a way that direct physical contact between the dielectric surface of the piston's active segment and that of the sleeve—a major wear factor for such a piston and sleeve set in prior art SCM flow cells—is completely eliminated.

A further object of the present invention is to provide such a flow cell with at least two electrodes variously configured so as to exhibit a high degree of conductivity and mounted in such a way that each of them contacts the sample flow stream just outside of a region within the flow cell where close-fitting dielectric surfaces slide past each other during use, so that the chances of the piston, as it reciprocates, making plastic-to-metal contact with such an electrode are virtually nil.

A still further object of the present invention is to provide such a flow cell in which the piston defines a narrow, elongated waist configured so as to allow the waist to give or, alternately, vibrate slightly about its juncture with the piston's active segment, thus not only augmenting the piston's reciprocating movements, but also increasing its usefulness as a mixer capable of significantly reducing the buildup of streaming current test signal degrading/weakening floc on electrode surfaces, as well as on immobile dielectric surfaces proximate with them, when such surfaces are exposed to a substantial portion of the overall test flow stream moving through the flow cell.

The intent of the present invention is also to provide for a SCM flow cell which has at least one piston-centering guide/bushing that is disposed contiguous with the sleeve and is aligned serially therewith, but which defines a narrower bore than that of the sleeve, with the spacing between the guide/bushing's inner cylindrical sidewall and the piston's active segment, in assembled relation, being too small for larger colloidal and grit particles to be sucked therethrough, thus keeping particulate matter known to scratch/gouge dielectric surfaces out of the piston/sleeve flow channel.

Another object of the present invention is to provide for a SCM flow cell that has such a piston-centering guide/bushing with said narrower bore as well as a large, generally flat, annular electrode mounted atop the guide/bushing and set well back from its upper edge, with the flow cell also employing a piston that defines a narrow, elongated waist, a system capable of clearing away, with each downstroke of the piston, any particulate matter, whether blocked from entering the narrow gap between the guide/bushing's inner cylindrical sidewall because of its size or simply clinging to said setback contiguous with the narrow gap's entrance.

Accordingly, there is provided a very wear resistant and reliable flow cell for the on-line measurement of the streaming current in water or wastewater that can be operated over long periods of time, nearly continuously, without having to be shut down for either cleaning or repair/replacement of critical parts. The flow cell includes a housing, an elongated hollow sleeve for slideably receiving a reciprocating piston-with-waist, the piston itself, and a retaining fitting/lower electrode assembly. The retaining fitting is a closure plug threadedly engageable with internal threads formed within the housing's lower end. Fabricated as an integral part of the housing, on the other hand, is a piston-centering guide/bushing that, in assembled relation with the piston, closely encircles short portions of the piston's active segment near its upper end, at the same time this guide/bushing forms both a stop for the sleeve's upper end and a shoulder atop which the upper—as well as by far the larger—of the flow cell's two sensing electrodes is mounted. Configured in the shape of an annular disc with a central opening of noticeably greater inner diameter than that of guide/bushing's active segment-encircling inner sidewall, the generally flat-faced upper electrode preferably has a surface area over six times larger than that of a prior art ring electrode having the same inner diameter, thus giving the upper electrode, in particular, a degree of conductivity heightened by an order of magnitude over that of said ring electrode.

The housing further defines a transverse passageway fluidly connected to both the piston-centering guide/bushing's inner cylindrical sidewall and to the sleeve. As the piston reciprocates, samples of a test flow stream directed through the transverse passageway, are alternately sucked downwardly into and then expelled upwardly from two conjoined flow channels of capillary width, the narrower one of which is short and formed between the piston's active segment near its upper end and the guide/bushing's inner cylindrical sidewall and the other of which is elongated and formed between the rest of the active segment and the sleeve. The upper of these two serially aligned flow channels is narrow enough that it blocks larger particles including grit as well as a sizeable fraction tion of the colloidal particles suspended in each sample of the test flow stream—from gaining access to the piston/sleeve flow channel. In order to prevent a buildup of signal degrading/weakening particulate matter at the entrance to the upper of these conjoined flow channels and atop an annular setback contiguous with said entrance—with the setback being so located to insure that the upper electrode's inner edge is kept spaced well apart from the piston, a self-cleaning system is engaged with every downstroke of the piston. This system's peak performance is contingent upon limiting the piston's downward travel—which preferably covers a distance of only ¼ inch over every ¼ second long cycle—in such a way that a piston-defined shoulder at the base of the waist/the active segment's upper end is brought just flush, at the bottom of each downstroke, with the upper electrode's annular flat face.

Once first and second ball valves fluidly connected to the housing's inlet and outlet ports, respectively, at the transverse passageway's distal ends have been temporarily shut off, an operator has then performed all of the basic steps needed to take the improved SCM flow cell off-line and transform it into a combination fluid retention receptacle/piston-with-waist powered mixing chamber. A cleaning fluid, rinse, or even an electrokinetically stable calibration solution can then be introduced and captured within the flow cell while leaving intact the plumbing used for fluidly connecting the flow cell to the test flow stream. Depending upon the task to be carried out, one may inject such a special purpose fluid directly into the receptacle/mixing chamber through either a small, housing-defined titration port or, alternately, the open outer end of an upturned 90 degree elbow on a housing-mounted, slueable fitting. Nevertheless, because in the case of the improved flow cell, those factors that give rise to physical wear which alters the gap-size of the piston/sleeve flow channel have been minimized to the extent they have been, said flow cell, provided it is cleaned on a routine basis, has much less need over time than do prior art flow cells to be either recalibrated with any such calibration solution and/or adjusted with the use of electronic compensation. Indeed, the preferred approach is to replace the improved flow cell's signal-generating components, including its electrodes, piston and sleeve—each of which is independently removable of the others herein listed—as preventive maintenance without having to do electronic compensation after the initial installation. This approach is based on a simple reality: the time period between any such field replacements in the case of the flow cell according to the present invention is likely to extend well beyond that of any prior art flow cell.

BRIEF DESCRIPTION OF THE DRAWINGS

Further details are explained below with the help of the examples illustrated in the attached drawings in which.

DETAILED DESCRIPTION OF THE PREFERRED EMBODIMENT

In the drawings and indicated generally by the reference numeral 10 is a streaming current detector which comprises an improved SCM flow cell in accordance with the present invention. With it, a user can measure the average net ionic and colloidal surface charge on the dielectric surfaces of a pair of conjoined annuli that are serially aligned, but differ from each other in their respective gap sizes, with the annulus which has the smaller gap size being defined by two dielectric materials unlike in their wear resistant properties, the charge so measured being a function of the charge influencing species, such as ions, charged molecules or colloidal particles, which are present in a liquid stream in flowing contact with said dielectric surfaces.

As illustrated in FIGS. 1 through 3 and 7, the SCM flow cell comprises a housing 20, a piston 11, a guide 42 with a threaded end 49 to which the piston is removably attached, a removable sleeve 16, a disc-like, annular upper electrode 15, and a removable, dual function retaining fitting/electrode assembly 21 atop and on the underside of which are mounted a disc-like lower electrode 14 and a coaxial cable coupler 29, respectively.

Figures 7, 8, 9:
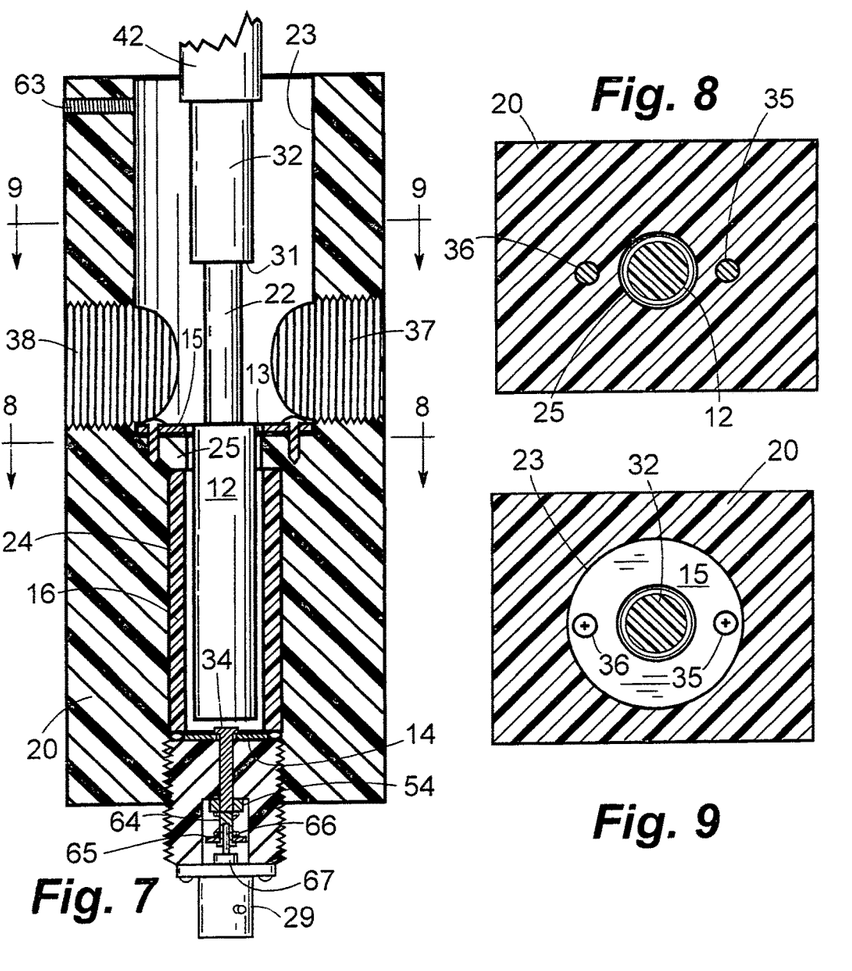
FIG. 7 is a longitudinal cross-section of the SCM flow cell according to FIG. 2, but with the piston, a fragment of the guide via which the piston interacts with the cam, and the coaxial coupler being included, while the coaxial cable and both of the isolation valves, as well as their respective threaded fittings, have been disconnected from the coupler and from the housing's inlet and outlet ports, respectively, and wherein the piston is depicted at the bottom dead center of its stroke.
FIG. 8 is a cross-section 8-8 through the SCM flow cell in FIG. 7.
FIG. 9 is a cross-section 9-9 through the SCM flow cell in FIG. 7.
Figure 10:
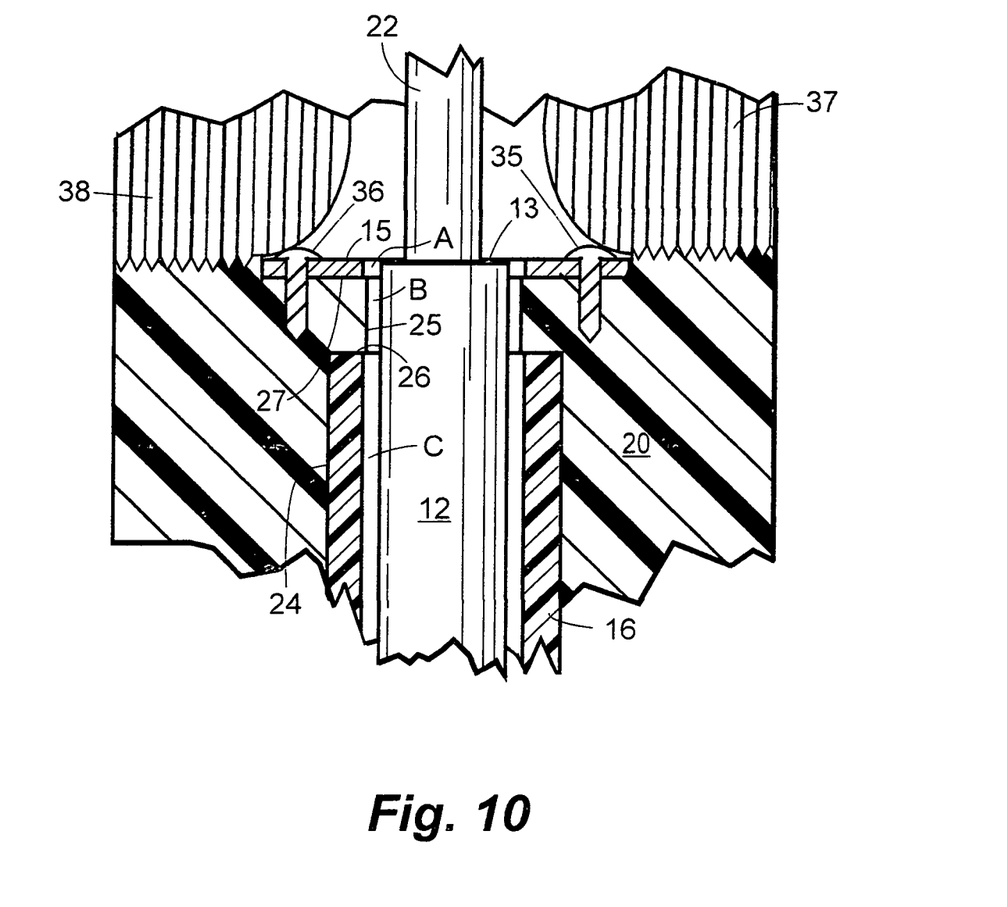
FIG. 10 is a fragmentary portion of the longitudinal cross-section, on an enlarged scale, of the SCM flow cell according to FIG. 2, with a fragment of the piston, likewise so enlarged, showing that the clearance between the piston's active segment and the flow cell's piston-centering guide is less that that which the piston's active segment encounters anywhere else in the flow cell.
Figures 11, 12, 13, 14:
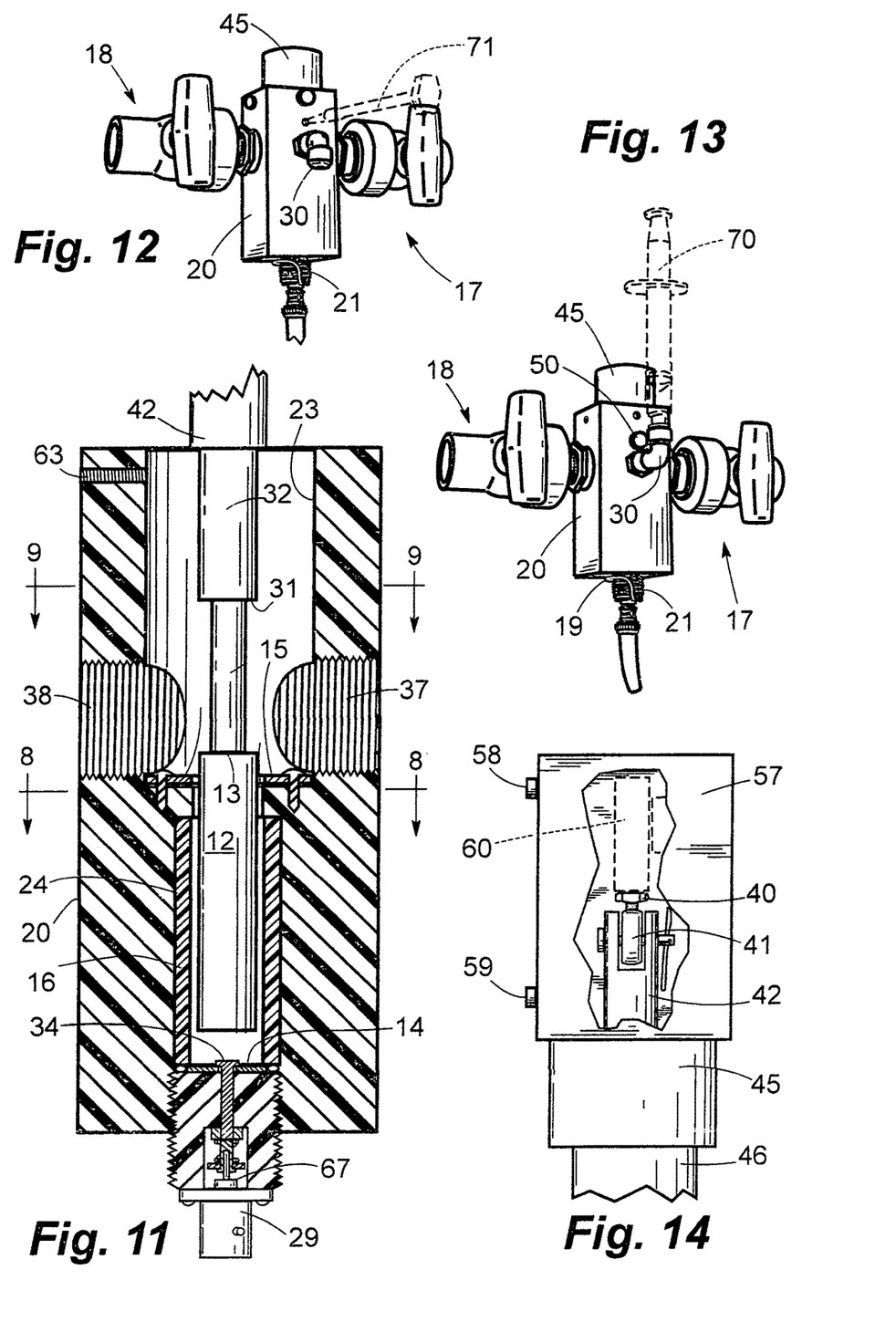
FIG. 11 is a longitudinal cross-section of the SCM flow cell according to FIG. 2, but with the piston, a fragment of the guide/pushrod that interacts with the cam, and the coaxial coupler being included, while the coaxial cable itself and both of the isolation valves, as well as their respective threaded fittings, have been disconnected from the coupler and from the housing's inlet and outlet ports, respectively, and wherein the piston is depicted at the top dead center of its stroke.
FIG. 12 is a left side perspective view, on a reduced scale, of the assembled SCM flow cell according to FIG. 1, as well as of a fragment of one end of a coaxial cable positioned to make electrical contact with terminals on the flow cell's retaining fitting, wherein a small syringe is shown aimed in the direction of an open, housing-defined, titration port, otherwise closed by an easily removable thumbscrew, with the syringe being depicted in dashed lines for illustrative purposes only and forming no part of the invention.
FIG. 13 is a left side perspective view, on a reduced scale, of the assembled SCM flow cell according to FIG. 1, as well as of a fragment of one end of a coaxial cable positioned to make electrical contact with terminals on the retaining fitting, wherein a large syringe is shown aimed in the direction of an opening at one end of an upwardly turned swivel port fluidly connected to a transverse passageway defined by the flow cell's housing and disposed between its inlet and outlet ports, with the large syringe being depicted in dashed lines for illustrative purposes and forming no part of the invention.
FIG. 14 is a frontal view, on an enlarged scale and partially cutaway, of the assembled mounting structure according to FIG. 2 and of a fragment of the support bushing affixed to the mounting structure's cylindrically-shaped upright, with the cutaway showing components of a spherical bearing mechanism that includes an adjustable walking nut for slideably engaging the cam, with said components being mounted at the upper end of the guide while the piston (not shown) is threadedly attached to the guide's lower end during use, with the cam being shown in dashed lines for illustrative purposes only and forming no part of the invention.

The housing 20 is preferably made from graphite-impregnated, low friction grade polyoxymethylene (Black Delrin) due to its dielectric properties, low surface friction coefficient, low surface adsorption and ease in machining. In addition to a generally horizontally oriented transverse passageway which fluidly interconnects the flow cell's threaded inlet and outlet ports 37, 38, the housing 20 defines an elongated, upper cylindrical inner wall 23, an elongated, lower cylindrical bore 24 and, juxtaposed in between them, an approximately inch thick annular shelf/piston-centering guide 25 (FIGS. 7, 10 and 11). Moreover, the inner wall 23, the shelf/guide 25 and the bore 24 are serially aligned with each other, with the through axis of each of them being oriented perpendicularly to that of the transverse passageway.

Located at the base of the cylindrical inner wall 23 and just below the transverse passageway's invert is a wide shoulder 27 defined by the shelf/guide 25. With this shoulder so located and with it, by design, sized to be just large enough to hold—with the use of screws 35, 36—the upper electrode 15 in place atop the shelf/guide 25, a test flow stream, as it moves through the transverse passageway, can continually wash the electrode's exposed upper face.

Figure 1:
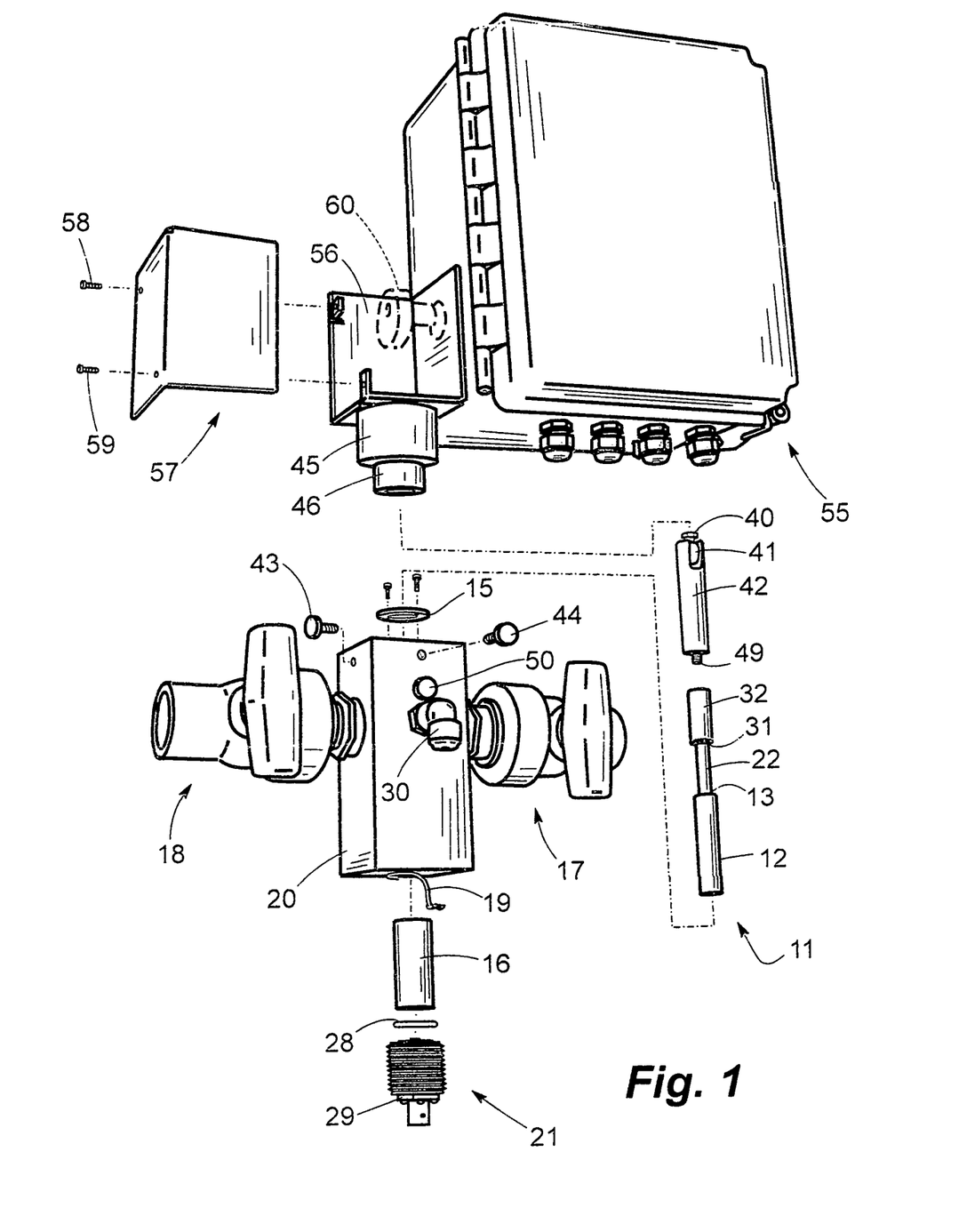
FIG. 1 is an exploded view of the improved streaming current measurement (SCM) flow cell and of a mounting structure for it, the flow cell being shown with removable sleeve, piston and electrodes, as well as with a swivel port rotatably connected to the flow cell's housing and a pair of isolation valves that threadedly engage it, the housing being depicted in a state in which it has been disconnected from a part of the mounting structure that is fixedly attached to an outer wall of a protective casing for a synchronous motor and an electronic circuit board (not shown), with a cam to reciprocate the piston being shown in dashed lines for illustrative purposes only and forming no part of the invention.

A narrow shoulder 26, also defined by the shelf/guide 25 but situated approximately ¼ inch below the wide shoulder 27, serves as a stop against which the upper end of the sleeve 16, once it has been slideably inserted as far as possible into the lower cylindrical bore 24 and brought into abutment with this stop, is then held in position there by the retaining fitting 21 (FIGS. 1, 7 and 11). Engageable with internal threads on the housing 20, the retaining fitting 21, when tightened thereon, compresses an O-ring 28 against the sleeve 16, forming a leaktight seal between the fitting and the housing 20.

In assembled relation, the sleeve 16 slideably receives the piston's active segment 12. Both the sleeve 16 and the active segment 12 are preferably fabricated of the same dielectric material, but one such as polytetrafluorethylene (Teflon) that is less wear resistant than that from which the shelf/piston-centering guide 25, an integral part of the housing 20 in the preferred embodiment, is formed. Moreover, the active segment 12 has a precision outer surface; and both the sleeve 16 and the inner cylindrical sidewall of the shelf/guide 25 have precision inner surfaces as well. In addition, the upper electrode 15, preferably a wafer-thin, stainless steel annular disc, has a precision inner edge. By way of a specific example, when the active segment's diameter measures 0.500 inch, the inside diameter of the upper electrode 15 and that of the sleeve 16 preferably measure 0.510 inch and 0.507 inch, respectively, with the inside diameter of the shelf/piston-centering guide's inner cylindrical sidewall being only 0.505 inch.

Thus, the respective gap-sizes of the conjoined annuli in the improved SCM flow cell differ from each other by a factor of 1.4, with an elongated annulus defined by the active segment 12 and the sleeve 16 having a substantially larger gap-size than does a much shorter annulus situated between the active segment and the shelf/guide 25. Moreover, as pointed out in FIG. 10 by reference characters A, B, and C, annular clearances vary markedly between regions on the active segment's surface and which one of the three serially aligned annular surfaces—whether it is that of the upper electrode 15 (clearance A), the shelf/guide 25 (clearance B) or the sleeve 16 (clearance C)—may be encircling a particular region on said surface at any given instant.

During upstrokes of the piston 11, not only are samples of the test flow stream sucked into the narrow, conjoined annuli of capillary width formed, in serial fashion, between the upper end of the active segment 12 and the inch tall inner cylindrical sidewall of the shelf/guide 25 and next between the rest of the active segment and the sleeve 16, but also the piston's waist 22 is momentarily raised upwardly by approximately ¼ inch (FIG. 11). Consequently, during down-strokes—almost instantaneously thereafter, fluid samples are expelled at the same time the waist's lower shoulder 13 is brought flush with the upper electrode's expansive top surface (FIG. 7).

Thus, such samples, as they are being expelled, can collide with a portion of the test flow stream swept along by the waist's upper shoulder 31 each time the reciprocating piston 11 plunges downwardly—that is, once every ¼th second in the preferred embodiment. The resultant turbulence, coupled with a scouring action on the part of those remnants of said portion that continue in motion—even after the piston 11 has momentarily hit the bottom dead center of its trajectory—only to then rapidly fan out across the upper electrode's exposed surfaces, helps to prevent a buildup of floc and other particulate matter there as well as on the upper annular edge of the shelf/guide's shoulder 27. Indeed, without such turbulence/scouring, this upper annular edge—from which the upper electrode's inner edge has been set well back as can be seen in FIG. 10—would incur a rapid buildup of signal-degrading floc during use.

Spaced apart from the upper electrode 15 by a distance greater than the combined spans of the shelf/guide's cylindrical inner sidewall and the sleeve 16 along their respective through axes, the lower electrode 14 is mounted so that it contacts samples of the test flow stream, sucked into the improved flow cell's conjoined annuli, just below the region where the active segment 12 slideably engages the sleeve 16 (FIGS. 7 and 11). Preferably, the lower electrode 14 is embodied in a stainless steel, circularly-shaped disc, the diameter of which is slightly larger than the inside diameter of the sleeve 16.

A screw 34, which threadedly engages a nut 54 so as to secure the disc 14 atop the retaining fitting/lower electrode assembly 21, is also, like this nut, one part of a multicomponent electrical connector that runs between the lower electrode and the coaxial cable coupler's pin 39. As shown in FIGS. 7 and 11, additional components of this electrical connector include an elongated gold wire, surrounded at its base by a Teflon collar 67 as both of them emerge, from the backside of the coaxial cable coupler's metal plate and into a retaining fitting-defined cavity which this metal plate, by design, completely covers. Electrical continuity between the nut 54 and this elongated gold wire—which terminates distally from the nut in the gold pin 39—is achieved with the use of a gold extension 64. In this key component, a closed-ended, tube-like member is joined to the center of a generally circular base from which the tube-like member extends perpendicularly, with a bore defined by both the base and a portion of the tube-like member contiguous with it being sized to slideably receive the elongated gold wire's free end. Providing structure to maintain reliable electrical contact between this free end and the tube-like member's closed end, as well as between this closed end and the nut 54, are a washer 65 and a stainless steel spring 66, both of which, in assembled relation, encircle the tube-like member, with the washer being mounted on top of the gold extension's circular base, thus effectively extending its outer periphery radially, at the same time the spring is being compressed between the washer and the nut.

Figure 2:
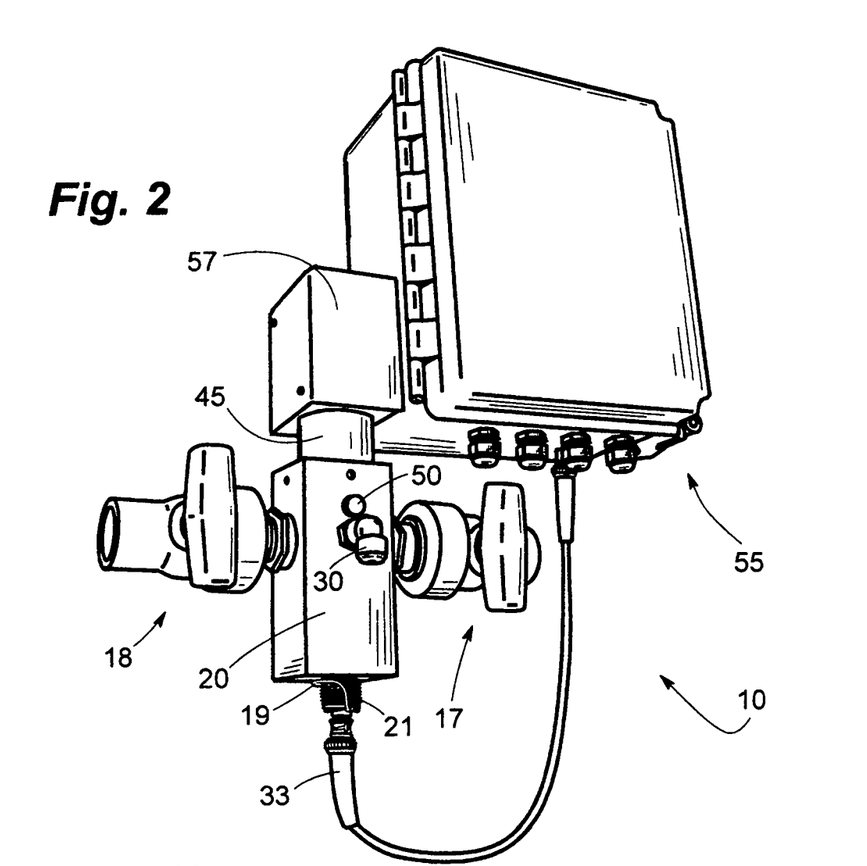
FIG. 2 is a left side perspective view of the assembled SCM flow cell and of the assembled mounting structure for this flow cell according to FIG. 1, and of a coaxial cable, the distal ends of which are positioned, respectively, to make electrical contact with terminals on the flow cell's retaining fitting and with connectors mounted on the protective casing's underside that are wired to the electronic circuit board.
Figure 3:
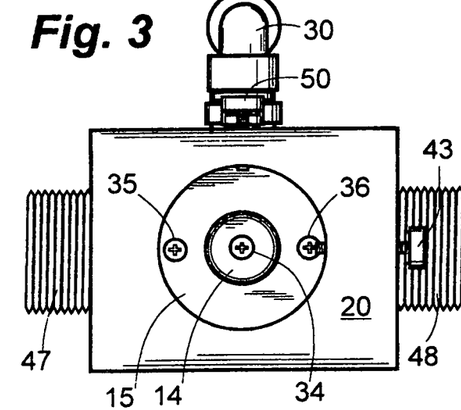
FIG. 3 is a top plan view, on an enlarged-scale, of the improved SCM flow cell according to FIG. 2, wherein the piston has been removed from the flow cell and the isolation valves have been disengaged from its housing, with both the upper and lower disc-like electrodes being visible in this drawing.
Figure 4:
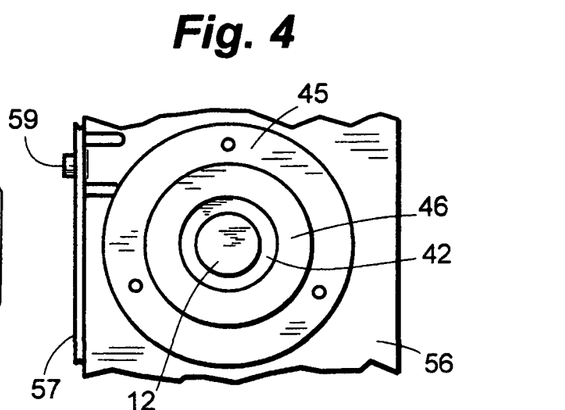
FIG. 4 is a bottom plan view, on an enlarged scale, that shows the underside of a fragmentary portion of the mounting structure according to FIG. 1, along with this mounting structure's cylindrically-shaped upright; the annular faces of a support bushing affixed to the upright and of a guide that not only slideably engages the support bushing but also interacts with the cam to reciprocate the piston; and concentric with these annular faces, the lower end of the piston itself, freed from the confines of the SCM flow cell's housing.
Figure 5:
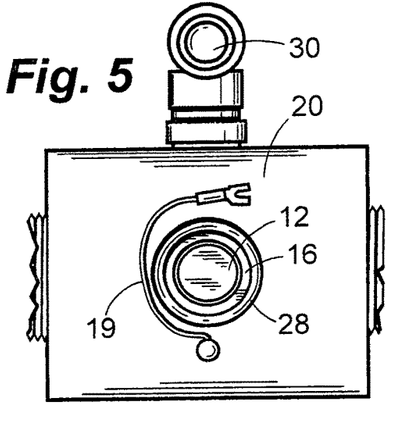
FIG. 5 is a bottom plan view, on an enlarged scale, that shows the improved SCM flow cell according to FIG. 2, when not only has the retaining fitting atop which the disc-like lower electrode is mounted been distanced from the flow cell, but also its isolation valves and all but a few fragmentary portions of the threaded fittings that otherwise connect them to the flow cell's housing have been removed as well.
Figure 6:
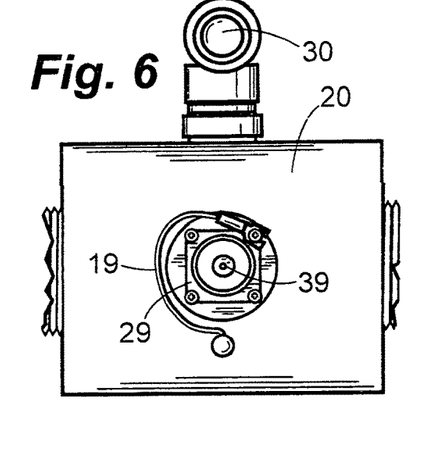
FIG. 6 is a bottom plan view, on an enlarged scale, that shows the improved SCM flow cell according to FIG. 2, when the combination retaining fitting and removable lower electrode assembly is threadedly engaged by the flow cell's housing at the same time a pigtail of the upper electrode's lead wire is secured to, and makes electrical contact with, a metal plate for a coaxial cable coupler affixed to the retaining fitting, with the coaxial cable itself disconnected from the coupler and the isolation valves disengaged from the threaded fittings that otherwise connect them to the flow cell's housing, wherein the drawing shows only fragmentary portions of these threaded fittings.

The upper electrode 15, on the other hand, is electrically connected to the coaxial cable coupler's metal plate by way of a lead wire 19 which terminates distally from the electrode in a pigtail (FIG. 6). Importantly, the improved flow cell has only this one pigtail, thus allowing an operator, in the process of reconnecting the lead wire 19, to do so—following the removal of the retaining fitting/lower electrode assembly 21 and its subsequent replacement or the like—with the reassurance that he has not inadvertently reversed the polarity of the streaming current raw signal when he feeds it, via a coaxial cable 33, from the coupler 29 to control and indicating circuitry (not shown) housed within protective casing 55 (FIG. 2).

Inspection and replacement of the piston 11 or, alternately, of the upper electrode 15, as well as of the housing 20 itself, is accomplished by first disengaging pinch bolts 43, 44, each of which is otherwise threadedly engaged with a hole 63 or the like formed therein (FIGS. 1,7 and 11). Once the pinch bolts 43, 44 have been sufficiently disengaged, one can then remove the housing 20 from a cylindrically-shaped support bushing 46, the outer diameter of which is sized so that this bushing can be slideably withdrawn from the housing's cylindrical inner wall 23. Prior to use, the housing 20 is slip fitted onto the support bushing 46 until the housing abuts a shoulder formed between the bushing and a cylindrically-shaped upright 45 which, like it, is part of a mounting structure within which a rotatable cam 60—but not the electric motor driving it—is located (FIGS. 1, 2 and 14).

The dimensions of the support bushing's inner sidewall, on the other hand, are such that the bulk of the guide 42 can move back and forth within this bushing as the piston 11 reciprocates. Upwardly of the support bushing 46 and inside an enclosure defined by two three-sided structures 56, 57, one of which is affixed to the protective casing's outside and the other of which is held by screws 58, 59 in assembled relation with the one so affixed, the guide 42 terminates in a yoke for a spherical bearing 41 (FIG. 14). Positioned atop the spherical bearing's protective case and threadedly engaged therewith is an adjustable walking nut 40, which, during use, slideably engages the cam 60.

In order to avoid any metal-to-plastic contact between the piston 11 and the disc-like, lower electrode 14, as well as between the piston and the screw 34, a clearance of 0.1 inch is preferably maintained between the active segment's lowermost face and the low electrode/screw assembly's uppermost surface. Precise adjustments to this clearance can be made by varying the degree to which the walking nut 40 threadedly engages the spherical bearing's protective case (FIG. 14).

Acting through the guide 42 to force the piston 11 into repetitive upward and downward motions, the cam 60 is driven by a synchronous motor (not shown) at a constant rpm. This rotational speed is preferably 240 rpm. Coupled with each of the piston's otherwise straight up and down repetitive movements is a potentially wear-engendering, side-to-side swivel on the part of the piston's active segment 12. This phenomenon, well known to those skilled in the art of SCM flow cells, can be observed by simply reciprocating such a flow cell's piston in the open air, freed from any constraints an intact flow cell might impose.

Indeed, the applicant has found in the case of prior art flow cells which have a close-fitting, but flexible piston and sleeve set but lack the improved flow cell's piston-centering guide 25—which is not only serially aligned and positioned contiguous with the sleeve 16, but also encircles the piston's active segment 12 much more tightly than does the sleeve—that physical contact between such a prior art flow cell's piston and sleeve creates irregular and uneven surfaces, as well as diameters, on both the active segment and the sleeve's inner sidewall. Furthermore, his findings are that the greatest signs of wear due to this particular type of physical contact are concentrated on the upper and lower portions of the surfaces where these dielectric elements slideably engage each other. This uneven and irregular wear has been found to alter said portions of the dielectric elements' respective diameters, as measured with the use of digital calipers, by amounts in the range of 0.005 inch to 0.010 inch, with a change in diameter of 0.010 inch or greater generally being considered a post-wear gap-size. Such an assessment is consistent with the fact that once that much change in diameter has occurred, too great a loss in the overall sensitivity of the streaming current measurement which the flow cell can achieve with any piston and sleeve set so worn has been incurred for this loss to be restored with the use of electronic compensation. Thus, the piston and sleeve set's useful life is over. The improved flow cell, according to the present invention, on the other hand, completely eliminates any piston and sleeve wear caused by physical contact between the piston's active segment 12 and the sleeve 16.

In addition, because the clearance B (FIG. 10) between the piston and the shelf/guide's inner cylindrical sidewall is only 0.005 inch, it is thus narrow enough to limit the size of those particles which can actually be sucked, as part of a test sample, into the annulus/sensing region situated in between the sleeve 16 and the active segment 12. Specifically, only those particles which have a smaller diameter than the gap size of said annulus/sensing region gain access to it. As a consequence, various aspects of wear known to be created by larger particles—such as scratches and grooves in and along the piston and the sleeve's inner sidewall which can cause the streaming current measurement to drift or become unstable—are significantly reduced in the improved flow cell.

As far as the small particles which are present in the fluid of a typical sample are concerned, the degree of physical wear that can be attributed to them as compared to that caused by direct contact between the piston and the sleeve or, alternately, by particles large enough to scratch and make grooves in a flow cell's dielectric elements is minimal, as those skilled in the art of SCM flow cells have observed over time.

In view of the extent to which direct physical contact can enlarge the gap-size of certain portions—and not others—of the annulus defined by the dielectric elements in a prior art flow cell's close-fitting, but flexible piston and sleeve set, one might expect that the 0.002 inch difference in the diameters of the inner sidewalls of the piston-centering guide 25 and the sleeve 16 that exists at the juncture between the improved flow cell's conjoined annuli would have little, if any, noticeable impact on such a flow cell's raw streaming current signal. Indeed, that might have been proven to be the case except for the fact that the applicant, through trial and error, found that a piston-with-waist has an optimum flexibility which, depending upon the configuration of the particular flow cell involved and that of its piston, can improve said signal.

As is best illustrated in FIGS. 7 and 11, the piston 11 defines, in addition to an upper boss 32 and the active segment 12, an elongated, narrow, cylindrically-shaped waist 32 which, like both the upper boss and the active segment, is an integral part of a unitary, flexible plastic structure, preferably fabricated of Teflon. Serially aligned with the upper boss and the active segment and disposed in between them, the waist has approximately the same length as does the upper boss; but together the upper boss and the waist take up only about one-half of the piston's overall length. Coupled with the waist's location and the fact that the waist has a diameter of only approximately 5/16th inch so that its tranverse cross-section area is slightly less than 40 percent of that of either the upper boss or the active segment, the piston 11, in the preferred embodiment, is configured so that the waist 22 can give and/or vibrate slightly and, in so doing, augment the piston's reciprocating movements, effectively and smoothly transporting test samples into and out of the improved flow cell's conjoined annuli.

However the piston's waist 22 and its active segment 12 do in fact interact, the improved flow cell's level of response has been proven to be superior, both in terms of the strength and uniformity of this flow cell's raw streaming current signal and of a substantially reduced requirement for electronic compensation over time. Indeed, the improved flow cell's level of response cannot be matched by any prior art flow cell with a flexible, but close-fitting piston and sleeve set—even such a flow cell in its "original" condition—unless the latter flow cell's response is augmented with the use of electronic compensation.

Means for generating a square wave signal as a crankshaft for the cam 60 is being rotated is described in U.S. Pat. No. 4,769,608. A square wave signal is used to facilitate the detection of an alternating current generated when the bulk of the active segment 12 slides back and forth within the sleeve 16, repeatedly advancing toward and then retreating from the lower electrode 14, at the same time the bulk of the active segment is retreating from and then advancing toward the upper electrode 15.

As an end of the active segment 12 of the piston 11 moves closer to the electrode 14, for example, an additional charge is induced thereon. An alternating current is generated at the frequency of the reciprocating piston 11. Means, including a filtering and synchronized measurement circuit, for processing this alternating signal, also known as the streaming current, so as to provide input to an indicating and control circuit (not shown) is disclosed in U.S. Pat. No. 4,769,608.

In keeping with a design paradigm in which many of the improved SCM flow cell's elements are at least dual function and even multi-functional in nature, the housing 20 preferably defines, in addition to the threaded inlet and outlet ports 37, 38 which the transverse passageway fluidly interconnects, a swivel port and a titration port, both of which are fluidly connected to the transverse passageway at its midsection. Moreover, the lower one of these two ports is threadedly engaged by a swivel-with-90 degree elbow fitting 30—preferably with a ¼ NPT, while a thumbscrew 50—preferably an 8/32 thumbscrew, colored red to make it easily identifiable—when it is engaged with the upper port is being used to close it (FIGS. 1-3, 12 and 13). Closure of the fitting 30, on the other hand, is preferably accomplished by threadedly engaging a male plug or the like with the fitting 30 at the outer end of its 90 degree elbow. Complementing the swivel and titration ports so that the improved flow cell can be used in an off-line (batch) mode are leaktight joints made with the use of threaded pipe fittings 47, 48 as they fluidly interconnect ball valves 17, 18 to the inlet and outlet ports 37, 38, respectively. With the housing 20 and the ball valves 17, 18 thus joined, a user is then free, with the flip of a handle atop each of these ball valves, to transform the transverse passageway and its two spaced apart, short extensions as defined by the pipe fittings 47, 48 into a combination fluid retention receptacle/piston-with-waist powered mixing chamber, accessible through the swivel port 30 and/or the titration port 50, as needed.

Whether the task which needs to be carried out entails cleaning, rinsing or even recalibrating the improved SCM flow cell, having the inlet ball valve 17 in place so that one can temporarily cut off flow into the flow cell from a dedicated test flow stream, quickly drain the flow cell's contents—if such is not needed for the task at hand—through the outlet ball valve 18, and then close it off as well, thus isolating the flow cell from said stream altogether represents a major game changer for many users. No longer does one have to remove the flow cell or dismantle plumbing in order to introduce and capture, within the flow cell, a special purpose fluid. Instead one can feed such a fluid, depending upon the quantity of it required, into the combination receptacle/mixing chamber with the use of a large syringe 70 inserted into the open outer end of the upturned 90 degree elbow on the fitting 30 or, alternately, with the use of a small syringe 71 inserted into the titration port (FIGS. 12 and 13).

Included among such special purpose fluids are DDPM and PVSK, each of which is an electrokinetically stable calibration solution having a known "charge", as Dentel teaches in U.S. Pat. No. 5,220,283, and long recognized for its usefulness in calibrating SCM flow cells as well as in confirming proper operation of the equipment. Alternately, while the improved flow cell is being operated in the on-line mode—that is, with both ball valves 17, 18 open, users can dynamically test the improved flow cell's charge measurement—to learn quickly whether a charge reversal has occurred, for example—by simply adding oppositely charged fluid with a known "charge" density through either the titration or the swivel port of the improved flow cell. Previously, users had to adjust the full scale plant dosage for test purposes and potentially adversely affect the treatment process.

For purposes of titrating an unknown test fluid introduced and captured inside the improved flow cell, the 90 degree elbow of the fitting 30 can be pointed downwardly to allow excess sample to "gravity drain" so that a precise volume or aliquot can be left in the combination receptacle/mixing chamber for titration calculation accuracy. Thus, the improved flow cell's additional ports facilitate a titration technique which allows the user to calculate the "charge demand" of a treatment-by-coagulation type process; and the result can be used to predict the chemical dosage requirements on a plant scale. Prior art embodiments required dedicated automated systems which most water treatment plants have found to be cost prohibitive.

The dual purpose functionality of this improved multiport, SCM flow cell which, as tests confirm, can be used to manually measure samples of known and unknown charge including positive, negative and neutral liquid samples with accuracy and repeatability not only eliminates the need for a user to purchase a second instrument dedicated to batch mode/lab scale experiments, but also, unlike such instruments which are commercially available, can be readily switched back to making charge measurements on a routine basis.

The invention claimed is:

1. An apparatus for measuring the streaming current as a function of the electric charge condition in a test flow stream of a fluid containing electrical charge influencing species, the apparatus comprising:
 a) a housing having a transverse passageway through which the stream can flow, the housing defining a piston-centering guide with an inner cylindrical sidewall and further defining an elongated, cylindrical void disposed perpendicularly to the transverse passageway and spaced apart therefrom by the length of the piston-centering guide's inner cylindrical sidewall, wherein said sidewall's through centerline is aligned serially with the cylindrical void's longitudinal centerline;
 b) an elongated, hollow sleeve made of a dielectric material, the sleeve being disposed within the cylindrical void and slideably removable therefrom, the piston-centering guide's inner cylindrical sidewall fluidly interconnecting the sleeve to the transverse passageway;
 c) a retaining fitting for holding the sleeve in a fixed position within the housing with respect to the piston-centering guide;
 d) a reciprocating piston having an active segment which is fabricated of the same dielectric material as is the sleeve, the active segment having a transverse cross-section sized such that the segment slip fits into both the piston-centering guide and the sleeve, with the guide and the sleeve, in assembled relation, being disposed both in tandem and contiguous with each other and configured to simultaneously encircle different portions of the active segment during use, and wherein at the same time the active segment and the sleeve together form a first flow channel between the active segment and the sleeve, the guide's inner cylindrical sidewall and the active segment together form a second flow channel between the active segment and the piston-centering guide that is narrower than the first flow channel;
 e) lower and upper electrodes mounted within the housing and affixed atop the retaining fitting and the piston-centering guide, respectively, with the upper electrode being a generally flat-faced, annular disc that defines a central opening which is aligned concentrically with the inner cylindrical sidewall's upper edge and set back therefrom, said upper and lower electrodes being spaced apart by a distance greater than the longitudinal span between the sleeve's bottom edge and said sidewall's upper edge, both electrodes being disposed so as to be contacted by the fluid being sucked sequentially into the flow channels during the piston's upstroke and then expelled therefrom with the piston's downstroke;
 f) means for moving the reciprocating piston in the piston-centering guide and said sleeve in tandem therewith, so that the piston reciprocates at a constant frequency while the guide interacts with the active segment's upper end to center the piston and, in so doing, curtails the piston's intrinsic side-to-side movements, thus eliminating wear-engendering direct physical contact between the active segment's lower end and the sleeve's inner sidewall; and
 g) means coupled to said electrodes for detecting an alternating current flowing between said electrodes that is generated at the frequency of the reciprocating piston.

2. The apparatus according to claim 1, wherein the piston-centering guide is further characterized as being fabricated of a wear resistant dielectric material, thus embodying the guide's inner cylindrical side wall with bearing-like properties and minimizing a potential for the active segment's upper end to incur wear as the guide interacts with said upper end to center the piston.

3. The apparatus according to claim 1, wherein an annular clearance between the upper electrode's inner edge for said large central opening so set back from the inner cylindrical sidewall's upper edge and the piston's active segment is at least twice as great as an annular clearance between said upper edge and the active segment, thus freeing the piston from potential plastic-to-metal contact with the upper electrode's inner edge.

4. The apparatus according to claim 1, wherein the first flow channel is further characterized as being too narrow for colloidal particles of a particular size and grit carried with such particles in the test flow stream to be sucked, as part of a test sample, further into the first flow channel, thus keeping larger particles known to scratch/gouge flexible dielectric surfaces out of the first flow channel.

5. The apparatus according to claim 4, wherein the piston further defines a flexible, elongated, cylindrically-shaped waist which terminates downwardly in a lower shoulder at a juncture of the waist with an upper end of the active segment, and wherein, during the piston's reciprocation, the piston's downward travel is limited in such a way that when the piston momentarily hits a bottom dead center of the piston's trajectory, the waist's lower shoulder is brought flush with the upper electrode's generally flat upper face, thus creating a turbulence in the test flow stream which cleans away both particles blocked at an entrance of the first flow channel and floc clinging atop the piston-centering guide's exposed surface between the inner cylindrical sidewall's upper edge and the upper electrode's inner edge set back therefrom.

6. The apparatus according to claim 1, which further comprises first and second ball valves and a housing-mounted fitting that is fluidly connected to the transverse passageway, wherein the piston further defines a flexible, elongated, cylindrically-shaped waist which terminates downwardly in a lower shoulder at a juncture of the waist with an upper end of the active segment, and wherein the housing further defines inlet and outlet ports at the transverse passageway's distal ends to which the first and second ball valves are fluidly connected in such a way that the transverse passageway can be temporarily isolated from said test flow stream, thus transforming the housing into a combination fluid retention receptacle/mixing chamber powered by the piston, with the receptacle/mixing chamber being accessible through the house-mounted fitting, so that various fluids can be introduced therethrough, captured within the receptacle/mixing chamber, mixed together with any other fluids present therein by simply reciprocating the piston, and then measured, as a sample sucked from the test flow stream itself would be measured, to determine the streaming current of the fluid contained in the receptacle/mixing chamber.

\* \* \* \* \*